United States Patent [19]
Cami et al.

[11] Patent Number: 5,907,059
[45] Date of Patent: May 25, 1999

[54] PROCESS FOR THE PREPARATION OF MONOSODIUM GLUTAMATE

[75] Inventors: Pierre Cami, Nesle, Switzerland; Aharon Eyal, Jerusalem, Israel

[73] Assignees: Amylum Belgium N.V., Aalst, Belgium; A.E. Staley Manufacturing Company, Decatur, Ill.

[21] Appl. No.: 08/930,629

[22] PCT Filed: Apr. 4, 1996

[86] PCT No.: PCT/IB96/00286

§ 371 Date: Feb. 10, 1998

§ 102(e) Date: Feb. 10, 1998

[87] PCT Pub. No.: WO96/31459

PCT Pub. Date: Oct. 10, 1996

[30] Foreign Application Priority Data

Apr. 7, 1995 [IL] Israel ......................................... 113299

[51] Int. Cl.⁶ ................................................. C07C 229/00
[52] U.S. Cl. ............................................................. 562/573
[58] Field of Search ................................................. 562/573

[56] References Cited

U.S. PATENT DOCUMENTS

| | | | |
|---|---|---|---|
| 2,306,646 | 12/1942 | Shildneck | 260/534 |
| 2,584,731 | 2/1952 | Ogawa et al. | 99/16 |
| 2,905,711 | 9/1959 | Novak et al. | 260/533 |
| 3,360,555 | 12/1967 | Frump et al. | 260/534 |
| 3,655,746 | 4/1972 | Shiraishi et al. | 260/527 |
| 4,956,471 | 9/1990 | Ito et al. | 548/344 |

FOREIGN PATENT DOCUMENTS

| | | |
|---|---|---|
| 939573 | 10/1963 | United Kingdom . |
| 2 095 232 | 9/1982 | United Kingdom . |
| 2095232 | 9/1982 | United Kingdom . |
| 2 103 221 | 2/1983 | United Kingdom . |
| 2103221 | 2/1983 | United Kingdom . |
| 96/31459 | 10/1996 | WIPO . |

*Primary Examiner*—Samuel Barts
*Assistant Examiner*—Rosalynd Keys
*Attorney, Agent, or Firm*—Jacobson, Price, Holman & Stern, PLLC

[57] ABSTRACT

The invention provides a process for the preparation of monosodium glutamate from a fermentatively prepared solution containing monoammonium glutamate, the process comprising: a) contacting the solution containing monoammonium glutamate salt with a basic anion exchange resin of at least medium strength to split the salt, whereby glutamate anions attach to the anion exchanger and ammonia is released in the solution; b) subjecting the ammonia-containing solution to distillation, to recover volatile ammonia therefrom; c) contacting the glutamate-containing anion exchange resin with a sodium base solution to regenerate the basic anion exchanger and to directly form monosodium glutamate salt in solution; and d) crystallizing monosodium glutamate salt directly from the monosodium glutamate-containing solution, wherein the crystallized salt has a purity of at least 98%.

17 Claims, No Drawings

PROCESS FOR THE PREPARATION OF MONOSODIUM GLUTAMATE

The present invention relates to a process for the preparation of monosodium glutamate (hereinafter referred to as MSG) from a glutamic acid fermentation broth.

More particularly, the present invention relates to a process for the preparation of MSG from a fermentatively-prepared solution containing monoammonium glutamate.

MSG is a well-known food additive which has been used for decades and which is used today mainly in the Far East, with a consumption of about 800,000 tons annually. Because of the great demand for MSG, many processes have been developed and/or proposed for the preparation thereof.

Thus, e.g., U.S. Pat. Nos. 2,877,160 and 2,978,384 teach various fermentation processes for the production of glutamic acid; U.S. Pat. Nos. 2,773,001 and 2,947,666 teach such processes in conjunction with the use of strong cation exchange resins to absorb glutamic acid, which is then eluted with normal hydrochloric acid or with dilute ammonium hydroxide, respectively.

In 1967, U.S. Pat. No. 3,325,539 was published, in which there was described and claimed a method for separating glutamic acid and salts thereof from a fermentation broth containing the same and solid materials, which method comprises passing fermentation broth containing glutamic acid, salts thereof, and solid materials upflow through a bed of strongly acidic cation exchange resin on the hydrogen cycle at a rate sufficient to expand the bed between 1.05 and 1.6 times its original depth, thereby adsorbing glutamic acid on said resin; discontinuing the flow of fermentation broth over said resin; and eluting said adsorbed glutamic acid from said resin with a 0.5–2 N sodium hydroxide solution.

MSG production via adsorbing glutamic acid on an acidic cation exchanger, as suggested in U.S. Pat. No. 3,325,539, suffers from several disadvantages: (1) a high consumption of reagents, entailing production of large amounts of by-product salts; (2) using an acidic cation exchanger frequently results in crystallization of glutamic acid on the resin material (column 3, lines 18–20); (3) the cation exchanger adsorbs the glutamic acid as well as the cation bound to it, and the cations present as impurities in the fermentation liquor, mostly resulting from the carbohydrate feed. As a result, large volumes of the resin are required. In many cases, only about one-third of the total available cation exchange capacity is available for glutamic acid adsorption.

The reactions involved with the process using acidic cation exchangers to adsorb glutamic acid ($H_2G$) from an acidic solution and regeneration by a base are as follows:

| | |
|---|---|
| (1) $NH_3 + H_2G + NH_4HG$ | Neutralization in fermentation |
| (2) $NH_4HG + 2R^-H^+ + R^-NH_4^+ + R^-H_3G^+$ | |
| (3) $R^-H_3G^+ + 2NaOH + R^-Na^+ + NaHG + 2H_2O$ | |
| (4) $R^-Na^+ + R^-NH_4^+ + H_2SO_4 + 2R^-H^+ +$ ½ $Na_2SO_4$ + ½ $(NH_4)_2SO_4$ | |
| (5) $H_2G + 2NaOH + NH_3 + H_2SO_4 + NaHGA +$ ½ $Na_2SO_4$ + ½ $(NH_4)_2SO_4$ | |

Such a process doubles the consumption of extra base and acid values, and produces two equivalents of by-product salt per mole of the product. In fact, reagent consumption and by-product formation are even higher, as shown in U.S. Pat. No. 3,325,539. The MSG obtained in reaction (3) above is acidulated to pH=3.2 to crystallize the glutamic acid, which is then neutralized.

Five years later, in 1972, U.S. Pat. No. 3,655,746 was published, which describes the attempts to find a satisfactory process for producing MSG, as follows:

"Heretofore a number of processes have been proposed for the preparation of MSG from a glutamic acid fermentation broth, but those processes invariably involve the steps of allowing glutamic acid hydrochloride, calcium glutamate, zinc glutamate, ammonium glutamate or glutamic acid to crystallize from the broth, then recovering those crystals and subsequently neutralizing them with, for instance, sodium hydroxide or sodium carbonate to obtain MSG."

"Those processes not only require complicated steps, but also result in unsatisfactory yields. Aside from those processes, a process is known in which an organic solvent is used to directly allow MSG to crystallize from the broth, but the resulting crystals are so low in purity that they must require aftertreatment."

"While the conventional purification processes employing cation exchange resin involve the adsorption and desorption of glutamic acid itself on and from resins, the resin in the present invention is employed for the adsorption of impurities, which makes it possible to purify by far a greater quantity of broth per unit volume of the resin."

With this background in mind, U.S. Pat. No. 3,655,746 teaches and claims a process for producing MSG which comprises contacting a glutamic acid fermentation broth at a pH between about 5 and about 9 with an amount of 1 liter by wet volume of a strongly basic anion exchange resin relative to about 0.2 to 0.6 molecular equivalent at the anionic impurities contained in said broth; adding to the effluent from the resin a stoichiometric amount of sodium hydroxide relative to the glutamic acid contained therein; and recovering the crystals of MSG thus obtained.

As described in said patent, the resin is employed in an amount enough to substantially adsorb the soluble impurities in the broth, but not in such an excess as to adsorb glutamic acid itself.

U.S. Pat. No. 3,655,746 uses strongly basic anion exchangers to remove soluble anionic impurities and coloring matter from the fermentation liquor. However, cationic and neutral impurities, particularly non-fermentables, are left with the glutamic acid and interfere in the crystallization of pure MSG. As a result, "it is particularly suitable for the treatment of broth which is low in the concentration of impurities other than organic acids." (column 4, lines 28–33).

Today, more than twenty years later, the major commercial processes for producing MSG from a fermentation broth involve acidulation with a mineral acid to a pH of about 3.2 to form the mineral acid salt, followed by crystallization of glutamic acid. Said glutamic acid is then separated, purified through recrystallization, and then reacted with sodium hydroxide to produce MSG.

However, even the commercial processes used today suffer from many disadvantages and problems.

Thus, referring, e.g., to a known commercial process in which sulfuric acid is the mineral acid used, the reactions involved in the formation of MSG (NaHG) can be represented as follows:

| | | |
|---|---|---|
| (1) | $NH_3 + H_2G + NH_4HG$ | Neutralization in fermentation |
| (6) | $NH_4HGA + $ ½ $H_2SO_4 + H_2G +$ ½ $(NH_4)_2SO_4$ | Acidulation |
| (7) | $H_2G + NaOH + NaHGA$ | Reacting the acid with |

(8) $H_2G + NaOH + NH_3 + \frac{1}{2} H_2SO_4 \xrightarrow{NaOH} NaHG + \frac{1}{2} (NH_4)_2SO_4$ Producing a mole of MSG consumes, in addition to the base required, one mole of ammonia and an equivalent of sulfuric acid, and forms an equivalent amount of the by-product ammonium sulfate.

Thus, the process uses up reagents and is therefore either wasteful or expensive, since ammonium sulfate is not a high value fertilizer or desired side product, and crystallization of ammonium sulfate is expensive.

Secondly, the purity of the glutamic acid precipitating in acidulation by sulfuric acid is low. Recrystallization is required, involving in many cases a phase transformation from α to β. These operations hold up capacity, are expensive in energy consmption, and use reagents for pH adjustment. In addition, large recycles are involved, further increasing capacity hold-up and reagent consumption.

Other disadvantages are related to the large volumes of ammonium sulfate solutions formed: the glutamic acid solubility in these solutions is high enough to cause major product losses; and crystallization of ammonium sulfate from this solution requires large crystallization capacity, as well as consuming large amounts of energy.

In a process described in the recent Japanese Patent 94017346, the fermentation liquor is treated with sulfuric acid to precipitate glutamic acid at the isoelectric point. The mother liquor is acidified to pH 1.5 by adding 95% $H_2SO_4$, and passed over a strongly acidic cation exchange resin to absorb glutamic acid. The absorbed glutamic acid is eluted with glutamic acid fermentation liquor containing urea, to prevent glutamic acid crystallization in the resin. The high consumption of reagent acids and bases, and the formation of low or negative value by-products, are not avoided, and an impurity addition is required. The latter entails the additional costs of a reagent and of urea removal from the product.

British Patent 811,688 and U.S. Pat. No. 2,921,002 recover glutamic acid from solutions comprising glutamic acid by absorption on anion exchangers. Said British patent describes a process for separating and concentrating glutamic acid from an aqueous liquid containing the same by a series of treatments with ion exchangers. First, cation and anion exchangers are used to remove cationic and anionic impurities, respectively. Then the glutamic acid is absorbed on a weakly basic anion exchanger and eluted by a strong acid solution. A base is added to adjust the pH to 3.2, and glutamic acid is crystallized.

With some adjustment, the above-described process seems applicable also for the preparation of monosodium glutamate from a fermentatively prepared solution containing ammonium glutamate. The ammonia is bound first to a strongly acidic cation exchanger in its H form:

(1)  $NH_3 + H_2G + NH_4HG$   Neutralization in fermentation
(9)  $R^-H^+ + NH_4HG \rightarrow R^-NH_4^+ + H_2G$ The liberated glutamic acid is bound to a weakly basic anion exchanger:

$H_2G + R \rightarrow R \cdot H_2G$ (10)

and eluted with NaOH to form MSG-containing solution:

$R \cdot H_2G + NaOH \rightarrow R + NaHG$ (11)

The strongly acidic cation exchanger is regenerated by a strong acid, e.g., HCl:

$R^-NH_4^+ + HCl \rightarrow R^-H^+ + NH_4Cl$ (12)

The over-all process is:

$H_2G + NH_3 + NaOH + HCl \rightarrow NaHG + NH_4Cl$ (13)

This process consumes, per mole of MSG, a mole of ammonia and a mole of HCl; it produces a mole of $NH_4Cl$, a by-product of low or even negative value. Another disadvantage is the large volume to be processed, due to the low solubility of glutamic acid.

British Patent 2,103,221 relates to the removal of glutamic acid from a mixture of amino acids, using a strong anion exchange resin. However, said patent does not teach or suggest a commercial process for obtaining MSG of high purity.

With the above-described state of the art in mind, according to the present invention there is now provided a process for the preparation of monosodium glutamate from a fermentatively-prepared solution containing monoammonium glutamate, said process comprising (a) contacting said solution containing monoammonium glutamate salt with a basic anion exchange resin of at least medium strength to split said salt, whereby glutamate anions attach to said anion exchanger and ammonia is released in said solution; (b) subjecting said ammonia-containing solution to distillation, to recover volatile ammonia therefrom; (c) contacting said glutamate-containing anion exchange resin with a sodium base solution to regenerate said basic anion exchanger and to directly form monosodium glutamate salt in solution; and (d) crystallizing monosodium glutamate salt directly from said monosodium glutamate-containing solution, wherein said crystallized salt has a purity of at least 98%.

The term "medium strength basic anion exchange resin," as used herein, is intended to denote resins having an apparent basicity in the range of pKa of at least 8, preferably of at least 9, since it has been found that weakly basic anion exchangers having an apparent pKa of less than 8, preferably less than 9, are not suitable for use in the present invention to split ammonium glutamate, attach the glutamate and release ammonia.

As will be realized, the present process has many advantages over the processes of the prior art, both in cost and in efficiency.

As indicated above, as a result of step (a) there is obtained an anion exchange resin with glutamate attached thereto and a solution which contains the cation contaminants, the neutral contaminants, and ammonia. Since ammonia is the most volatile component of said solution, it is easily recovered for recycling.

Thus, in preferred embodiments of the present invention, the ammonia recovered by said distillation is recycled for the fermentative preparation of monoammonium glutamate.

In the aforementioned especially-preferred embodiment of the invention, the process as a whole, and step (c) in particular, is energy-efficient, since the strong basicity of a sodium base serves as the driving force to regenerate said basic anion exchanger for reuse, while eluting MSG in solution in relatively pure form, from which solution it can be readily crystallized in pure form.

Preferably, said sodium base is selected from the group consisting of sodium hydroxide, sodium carbonate and sodium bicarbonate, and in especially preferred embodiments of the present invention, there is provided a process for the preparation of monosodium glutamate from a fermentatively-prepared solution containing monoammonium glutamate, said process comprising (a) contacting said solution containing monoammonium glutamate salt with a basic anion exchange resin of at least medium strength in the hydroxide form to split said salt, whereby said glutamate attaches to said anion exchanger and ammonia is released in said solution; (b) subjecting said ammonia-containing solution to distillation, to recover volatile ammonia therefrom; (c) contacting said glutamate-containing anion exchange resin with a sodium hydroxide solution to regenerate said strong base anion exchanger and to directly form monosodium glutamate salt in solution; and (d) crystallizing monosodium glutamate salt directly from said monosodium glutamate-containing solution, wherein said crystallized salt has a purity of at least 98%.

Medium strength resins, such as Rohm and Haas' Amberlite IPA 67 and Duolite 374, Purolite's A 830, A 835 and A 845, Mitsubishi's Diaion 11 and Beyer's Lewatit S5428, are capable of partial splitting of ammonium glutamate. As the splitting progresses, the amount of ammonia released increases, and higher pH values are reached in the solution. Tertiary amine-based anion exchangers, however, lose their binding capacity at high pH. For completing the splitting of the salt (pH of about 12 or higher), a strongly basic anion exchanger is preferred. That is particularly true if $Na^+$ and $K^+$ are present as contaminants in the fermentation liquor. Suitable strongly basic anion exchangers are quaternary amine-based resins in their OH form, such as Amberlite 900, Amberlite 910, Duolite A1715, IRA 420 and Dow XUS-40196.00.

Therefore, a quaternary amine, strongly basic anion exchanger can be used as the sole salt-splitting anion exchanger in the system. It was found, however, that a combination of a weaker anion exchanger having an apparent pKa of at least 9, and a stronger anion exchanger, such as a quaternary amine strongly basic anion exchanger, is especially preferred.

Thus, in a preferred embodiment of the present invention, the monoammonium glutamate solution is contacted first with a medium strength basic anion exchanger to split a part of the salt, attach part of the glutamate, and release part of the ammonia. The effluent from this contact is then contacted with a more strongly basic quaternary amine anion exchanger for further splitting of the salt, attachment of glutamate, and release of ammonia. The ammonia-containing effluent from this contact, which is substantially free of glutamate, is subjected to distillation for recovery of volatile ammonia therefrom. The regenerating sodium base solution is contacted first with the quaternary amine basic anion exchanger and regenerates it. The effluent solution, containing the base and MSG or disodium glutamate, is used to regenerate the medium strength anion exchanger and to directly form monosodium glutamate salt in the solution.

The combination of a medium strength anion exchanger and a quaternary amine basic anion exchanger provides for practically complete glutamate recovery on the one hand, and regeneration without resorting to high over-all excess of sodium base on the other hand. The amount of sodium base introduced into the contact with the glutamate-containing, quaternary amine basic anion exchanger is equivalent to the glutamate attached to that resin plus that attached to the weaker resin. Therefore, there is high excess of sodium base in the contact with the quaternary amine basic anion exchanger, providing for highly efficient elution. The partially neutralized solution formed is used for the regeneration of the weaker anion exchanger, where a marked excess of base is not required. This scheme of operation is particularly advantageous when the salt splitting (step a) and the regeneration (step c) are performed in a counter-current flow. On the other hand, when $Na^+$ and $K^+$ contaminants are pre-removed before contact of the monoammonium glutamate solution with the basic anion exchanger, or when initial full recovery of glutamate values is not required, then a basic anion exchanger of medium strength can be used as the sole anion exchanger in the system.

A quite pure MSG solution is obtained in step (c). Yet some impurities may not be avoided in industrial operation, particularly if said fermentatively-prepared ammonium glutamate solution is highly contaminated. The crystallization in step (d) provides for the final purification. A bleed of mother liquor is required for removing impurities. This bleed contains just a small fraction of the glutamate, but still deserves a treatment for recovery of the glutamate values therefrom. There are several options for such treatment. The preferred option will be determined by the nature and content of impurities. A highly contaminated bleed can be treated through acidulation. Less contaminated bleeds can be sent upstream. Thus, e.g., said bleed can be used as a washing solution in ultrafiltration, or combined with the solution fed to step (a).

Due to the relative purity of said solution in preferred embodiments of the present invention, a part of the mother liquor remaining after the crystallization of MSG in step (d) can be combined with sodium hydroxide for use in step (c).

In especially preferred embodiments of the present invention, a part of the mother liquor remaining after crystallization of MSG in step (d) is combined with sodium hydroxide and filtered, prior to being used in step (c).

As will be understood, said fermentative preparation is of the type involving the consumption of carbohydrates and ammonia, and preferably includes a step of ultrafiltration to remove cells and other matter from the solution containing monoammonium glutamate before contact with said anion exchanger. Partial concentration of the solution after cell removal (e.g., via water distillation or reverse osmosis) is optional.

It is also possible to use the first step of the process of U.S. Pat. No. 3,655,746 as a pre-treatment step to remove anionic impurities before carrying out step (a) of the present invention. Alternatively, or in addition, active carbon, adsorbing resins, or ultra- or nano-filtration can be used for such pretreatment.

In accordance with another embodiment of the present invention, the contacting of the monoammonium glutamate with the anion exchange resin in step (a) is conducted under $CO_2$ pressure and the ammonia released in the solution is at least partially converted to ammonium carbonate.

In accordance with another aspect of the present invention, at least a part of the ammonia released in step (a) is distilled during the contacting of the monoammonium glutamate solution with the anion exchangers.

In accordance with yet another aspect of the present invention, at least part of the solution obtained in step (b) is contacted again with the basic anion exchanger.

While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

EXAMPLE 1

A fermentation broth with concentrations of 120 g/l of glutamic acid; 11 g/l of ammonium nitrogen and 16.9 g/l of organic nitrogen, was produced by fermentation of a beet molasses medium mixed with starch hydrolysate.

This solution was contaminated with sugars, due to incomplete fermentation; other non-fermentables; inorganic anions and cations resulting from the molasses, and from nutrients added to the fermentation; and with other fermentation products, such as carboxylic acids.

The bacteria cells and other suspended matter were removed by using ultrafiltration, and were washed by diafiltration with water. In the permeate, 99% of the glutamic acid of the initial broth was recovered.

Concentrations in the permeate were as follows: 95 g/l of glutamic acid; 8.7 g/l of ammonium nitrogen; 11.17 g/l of organic nitrogen. The transmittance of the permeate, measured at 750 nm, was 46%.

The above-described permeate was used in all of the examples included herein.

In Example 1, 4 liters of permeate were fed on a column of 1 liter of strong base resin exchanger IPA420 produced by Rohn & Haas, which is a type 1 quaternary amine in OH form. The column was washed with 2 liters of water, was then eluted with 3 liters of caustic soda solution (40 g/l of NaOH), and washed again with 2 liters of water. The glutamic acid and organic nitrogen were analysed in the eluate plus washing water. 30 g of glutamic acid and 4 g of organic nitrogen were measured in the eluate plus washing water.

The experiment was repeated, using IRA910 resin, which is also produced by Rohm & Haas, and is a type 2 quaternary amine, instead of IRA420. 32 g of glutamic acid and 5.5 g of organic nitrogen were measured in the eluate plus washing water.

EXAMPLE 2

10 liters of permeate were fed on a column of 1 liter of XE583 tertiary amine resin, which is produced by Rohm and Haas and is a tertiary amine, followed by 2 liters of washing water. The transmittance of the effluent, measured at 750 nm, was 87%, compared to 46% measured in the permeate.

5 liters of this effluent was fed on a 1 liter IRA420 OH form column. The column was washed with 2 liters of water and then eluted with 2 liters of caustic soda solution (80 g/l NaOH) and 2 liters of water.

70 g of glutamic acid and 6.7 g of organic nitrogen were measured in the eluate plus washing water.

On a second part of the XE583 treated effluent, a tertiary amine resin IRA67, produced by Rohm & Haas and having a pKa of 9.5, was used. Five liters of the effluent was fed on a 1 liter IRA67 column; the column was washed with 2 liters of water and then eluted with 2 liters of caustic soda solution (40 g/l NaOH) and 2 liters of water.

87 g of glutamic acid and 9 g of organic nitrogen were measured in the eluate plus washing water.

EXAMPLE 3

20 liters of the permeate were fed on a column of 1 liter of XE583 tertiary amine resin, followed by 2 liters of washing water. The transmittance of the effluent, measured at 750 nm, was 81%, compared to 46% measured in the permeate.

11.47 g of organic nitrogen was measured for 100 g of glutamic acid in the effluent. 10 liters of the effluent were fed on a 1 liter column of granular active carbon at 65° C. 11.2 g of organic nitrogen for 100 g of glutamic acid was measured in the effluent of the granular active carbon column.

5 liters of this effluent was fed on a 1 liter EXA36 primary amine resin column, produced by Mitsubishi Kasei. 10.9 g of organic nitrogen was measured for 100 g of glutamic acid in the effluent of the EXA column.

This last effluent was fed on a column of 1 liter IRA67 resin and 2 liters of washing water. The first fraction of effluent was distilled to recover the released ammonia. Virtually all the released ammonia was recovered on adding 0.5 g/l NaOH to the effluent.

The resin column was eluted with 2 liters of caustic soda (40 g/l NaOH). 10.2 g of organic nitrogen was measured for 100 g of glutamic acid in the eluate.

Examples 1–3 used large volumes of ultra-filtered fermentation broth to simulate the resin loading in a counter-current mode of operation. This operation scheme concentrates on the resin some impurities that in general operation are removed in the pre-treatment. The eluate is thus more contaminated than would be in actual practice. Yet it provides for recovering most of the MSG in a pure form through crystallization, as shown below in Example 4.

EXAMPLE 4

Example 3 was repeated, using IRA420 resin instead of IRA67. The IRA420 column was eluted with caustic soda (80 g/l NaOH).

A fraction of the eluate (pH=8) was neutralized with a small amount of pure glutamic acid to pH 7.2, concentrated by evaporation under reduced pressure at 60° C., and then cooled at 20° C. Most of the MSG crystallized at a nitrogen purity of 99%. The purity measured by polarization was higher than 98%.

EXAMPLE 5

Several weak and medium strength anion exchangers (none of them is a strong base quaternary amine) were compared by equilibration with solutions comprising ammonium glutamate or its mixtures with ammonia (the mixtures represent solutions after partial salt splitting). In equilibrium with ammonium glutamate solutions (the resin to aqueous solution volume ratio was small so that the salt splitting was small), the glutamate loading (equivalents per liter resin) were, in decreasing order:

| | |
|---|---|
| Amberlite IRA 67 (Rohm and Haas) | 1.5 |
| A 845 and A 830 (Purolite) | 1.35 |
| Diaion WA 11 (Mitsubishi) | 1.0 |
| Duolite A 374 (Rohm and Haas) | 0.9 |
| Diaion WA 30 (Mitsubishi) | 0.5 |

The above sequence indicates the sequence of resin capacity at the exit of a counter-current contact with many contact stages. It does not teach, however, the efficiency of salt splitting. For that purpose, the loading in contact with a solution representing partial salt splitting was determined. In equilibrium with a solution of pH=9 (representing 25% salt splitting), the loadings (eq/l) were:

| | |
|---|---|
| IRA 67, A 845, A 830 | about 0.4 |
| WA 11 and A 374 | about 0.2 |
| WA 30 | <0.05 |

These results could be interpreted to show that the apparent basicity in terms of pKa for WA 30 is lower than 9; for WA 11 and A 374 it is slightly higher than 9; and that for IRA 67, A 845 and A 830 it is significantly higher than 9. Additional equilibrations with solutions, representing salt splitting of 50–90%, show that at this range A 830 acts as the strongest resin among these medium strength resins.

EXAMPLE 6

Splitting of ammonium glutamate was tested on a continuous counter-current contacting with an anion exchanger of a medium strength.

The concentration of the glutamate salt in the solution was 0.8 eq/l. The resin was Purolite's A 830, described by the manufacturer as a macroporous, weak base acrylic resin, obtained and used in the free base form. The glutamate-carrying resin was eluted with an NaOH solution and sent back to contact the glutamate solution. The resin loading, in terms of equivalents of glutamate bound per liter resin, and the efficiency of salt splitting (the fraction of glutamate in the incoming solution that was bound to the resin) were determined. The flow rates in terms of solution volume per resin volume ranged between 0.7 and 2.4. For these flow rates, the resin loading ranged between 0.49 and 0.76 eq/l respectively, and the salt splitting between 86 and 39% respectively. Thus, at flow rate of 1.2, the resin loading was 0.63 eq/l and the salt splitting effiency was 66%. These results show that, using the medium strength anion exchanger, Purolite A 830, high salt splitting yields and good anion exchange capacity are obtainable.

EXAMPLE 7

The experiment of Example 6 was repeated, using Rohm and Haas' Amberlite IRA 67, described by the manufacturer as a macroreticular, weak base acrylic resin, obtained and used in the free base form. The flow rates range was 0.7 to 2.6. The loading ranged between 0.4 and 0.9 eq/l respectively, and the salt splitting efficiencies ranged between 70 and 40% respectively. At a flow rate of 1.6, the resin loading and the efficiency were 0.7 and 55% respectively. These results show that, using the medium strength anion exchanger Amberlite IRA 67, high salt splitting yields and good anion exchange capacity are attainable.

EXAMPLE 8

The experiments in Examples 6 and 7 were repeated, with two changes:

1) the feed was a solution comprising 0.25 eq/l ammonium glutamate and 0.5 eq/l ammonia, representing an ammonium glutamate solution after 67% salt splitting on a medium strength anion exchanger) and 2) the resin was a styrinic strong base anion exchanger, Rohm and Haas' Amberlite IRA 900.

At feed rates of 2.85 and 3.24, loadings of 0.71 and 0.81 eq/l were found. Glutamate adsorption from the solution is practically completed.

EXAMPLE 9

20 liters of the permeate were pretreated as in Example 3, using XE583 tertiary amine resin, granular active carbon and then EXA36 primary amine resin. The last effluent out of EXA36 resin was fed on a IRA67 column and its effluent on a IRA420 colum. Thereafter, water was fed for sweetening of the two colums. A total of 735 g of glutamic acid was loaded on the two columns, 400 g on the IRA67 and 335 g on the IRA420, measurement being effected on a sample of resin. The two columns were then eluted by 2.25 l of 80 g/l caustic soda solution, fed first on the IRA420 column, the effluent of which was then fed on the IRA67 column. Thereafter, water was fed for sweetening of the two columns. The final effluent, having a pH of 7.3, was concentrated by evaporation under reduced pressure at 65° C. for MSG crystallization. Crystallized MSG was separated from crystallization mother liquor and dried under vacuum.

350 g of MSG crystal, having a 99.5 purity, were obtained. Measured by polarization and nitrogen analysis, the crystallization yield was 47%.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. A process for the preparation of monosodium glutamate from a fermentatively-prepared solution containing monoammonium glutamate, said process comprising:

(a) contacting said solution containing monoammonium glutamate salt with a basic anion exchange resin having an apparent basicity in the range of pKa of at least 8 whereby glutamate anions attach to said anion exchanger and ammonia is released in said solution;

(b) subjecting said ammonia-containing solution to distillation, to recover volatile ammonia therefrom;

(c) contacting said glutamate-containing anion exchange resin with a sodium base solution to regenerate said basic anion exchanger and to directly form monosodium glutamate salt in solution; and (d) crystallizing monosodium glutamate salt directly from said monosodium glutamate-containing solution.

2. A process according to claim 1, wherein said crystallized salt has a purity of at least 98%.

3. A process according to claim 1, wherein said sodium base is selected from the group consisting of sodium hydroxide, sodium carbonate and sodium bicarbonate.

4. A process according to claim 1, wherein said sodium base is sodium hydroxide.

5. A process according to claim 1, wherein the ammonia recovered by said distillation is recycled for the fermentative preparation of monoammonium glutamate.

6. A process according to claim 1, wherein said fermentative preparation is of the type involving the consumption of carbohydrates and ammonia.

7. A process according to claim 1, wherein mother liquor remaining after the crystallization of monosodium glutamate in step (d) is combined with sodium hydroxide for use in step (c).

8. A process according to claim 1, wherein mother liquor remaining after crystallization of monosodium glutamate in step (d) is combined with sodium hydroxide and filtered, prior to being used in step (c).

9. A process according to claim 1, wherein said solution containing monoammonium glutamate salt is first contacted with a medium strength basic anion exchanger to split a part of said salt, attach part of said glutamate anions and release part of said ammonia, and then the effluent from said contact is contacted with a stronger quaternary amine basic anion exchanger for further splitting of said salt, attachment of said glutamate anions, and release of ammonia.

10. A process according to claim 9, wherein said ammonia-containing effluent, substantially free of glutamate anions, is subjected to distillation for recovery of volatile ammonia therefrom.

11. A process according to claim 9, wherein said regenerating sodium base solution is first contacted with said quaternary amine basic anion exchanger to regenerate the same, whereafter the resulting effluent solution is used to regenerate said medium strength basic anion exchanger and to directly form monosodium glutamate salt in said solution.

12. A process according to claim 1, wherein the contacting of the monoammonium glutamate with the anion exchange resin in step (a) is conducted under $CO_2$ pressure and the ammonia released in said solution is at least partially converted to ammonium carbonate.

13. A process according to claim 1, wherein at least a part of the ammonia released in step (a) is distilled during the contacting of the monoammonium glutamate solution with the anion exchangers.

14. A process according to claim 1, wherein at least part of the solution obtained in step (b) is contacted again with the basic anion exchanger.

15. A process according to claim 1, wherein contacting a solution comprising ammonium glutamate or a sodium base solution with the resin is conducted counter-currently.

16. A process according to claim 1, wherein said basic anion exchange resin has an apparent basicity in the range of pKa of at least 9.

17. A process according to claim 2, wherein said crystallized salt has a purity of at least 99%.

* * * * *